US011085042B2

(12) United States Patent
Kwok et al.

(10) Patent No.: US 11,085,042 B2
(45) Date of Patent: Aug. 10, 2021

(54) METHOD OF PRODUCING DNA AND DNA LIBRARY

(71) Applicant: City University of Hong Kong, Kowloon (HK)

(72) Inventors: Chun Kit Kwok, Kowloon (HK); Pui Yan Yeung, New Territories (HK)

(73) Assignee: City University of Hong Kong, Kowloon (HK)

( * ) Notice: Subject to any disclaimer, the term of this patent is extended or adjusted under 35 U.S.C. 154(b) by 565 days.

(21) Appl. No.: 15/957,037

(22) Filed: Apr. 19, 2018

(65) Prior Publication Data
US 2019/0323005 A1    Oct. 24, 2019

(51) Int. Cl.
*C12N 15/10*    (2006.01)
*G01N 27/26*    (2006.01)
*C02F 1/469*    (2006.01)

(52) U.S. Cl.
CPC .......... *C12N 15/1096* (2013.01); *C02F 1/469* (2013.01)

(58) Field of Classification Search
CPC .......... C12N 15/1096; C12Q 2521/107; C12Q 2521/319; C12Q 2527/125
See application file for complete search history.

(56) References Cited

U.S. PATENT DOCUMENTS

| 8,574,864 | B2 * | 11/2013 | Vaidyanathan | C12N 15/10 435/21 |
| 9,828,600 | B2 * | 11/2017 | Moore | C12N 15/1096 |
| 2015/0147785 | A1 * | 5/2015 | Seitz | C12Q 1/6858 435/91.52 |

FOREIGN PATENT DOCUMENTS

EP    0632134 A2 *    1/1995    ........... C12N 9/1252

OTHER PUBLICATIONS

Tips for Maximizing Ligation Efficiencies, New England BioLabs Inc., Mar. 19, 2016 (Year: 2016).*

* cited by examiner

*Primary Examiner* — Jeremy C Flinders
*Assistant Examiner* — Taryn Kimberly Wood
(74) *Attorney, Agent, or Firm* — Renner Kenner Greive Bobak Taylor & Weber (57) ABSTRACT

A method of producing a cDNA from a sample of nucleic acids includes the steps of: generating a dephosphorylated RNA from the sample; ligating the dephosphorylated RNA with a first adapter in the presence of a crowding agent to produce a ligated product; removing the excess first adapter by adding at least two enzymes; and performing reverse transcription in a lithium-containing buffer to produce the cDNA. A method of preparing a DNA library and a kit for such preparation are also disclosed.

19 Claims, 10 Drawing Sheets

Specification includes a Sequence Listing.

| Temperature: | 37°C | | | |
|---|---|---|---|---|
| Total PEG%: | 12.5 | | | |
| [N60 DNA] µM: | 0.1 | 0.1 | 0.1 | 0.1 |
| [5'-Adapter] µM: | 0.1 | 0.25 | 0.5 | 1 |

METHOD OF PRODUCING DNA AND DNA LIBRARY

SEQUENCE LISTING

The Sequence Listing file entitled "sequencelisting" having a size of 4,096 bytes and a creation date of Apr. 19, 2018, that was filed with the patent application is incorporated herein by reference in its entirety.

TECHNICAL FIELD

The present application relates to a method of producing a DNA in particular but not exclusively a cDNA. The present invention also pertains to a method of preparing a DNA library and a kit for doing so.

BACKGROUND OF THE INVENTION

Recovering RNAs from a naturally occurring source or pathogenic source is usually required in genome-wide studies. Understanding the RNA expression, RNA structure, RNA interaction, and RNA epigenetic features will provide insights on the cellular functions of the genes and the relationship between the RNA and the gene expression. The extracted RNA can be used as a template to produce a DNA in particular a cDNA for subsequent amplification so as to form a library for storage and analysis.

However, it could be very challenging to produce a cDNA from low-abundant-RNA, i.e. the RNA is presented in relatively low amount in its source. The typical RNA recovery methods and preparation of cDNA could lead to substantial loss of the gene material and are generally time-consuming. Also, one of the common methods for selecting the target RNAs from a reaction mixture is by using polyacrylamide gel. The preparation of the polyacrylamide gel can be time-consuming and is susceptible to contamination, which results in poor recovery yield and low production yield of the corresponding cDNA.

Therefore, there remains a strong need for a fast and economically-efficient approach for preparing a nucleic acid in particular a cDNA and its corresponding library such as for low-abundant RNAs.

SUMMARY OF THE INVENTION

The present invention in a first aspect provides a method of producing a DNA in particular a cDNA from a sample of nucleic acids, comprising the steps of:
  a) generating a dephosphorylated RNA from the sample;
  b) ligating the dephosphorylated RNA with a first adapter in the presence of a crowding agent to produce a ligated product;
  c) removing the excess first adapter by adding at least two enzymes; and
  d) performing reverse transcription in a lithium-containing buffer to produce the cDNA.

In an embodiment, the dephosphorylating agent comprises one or more alkaline phosphatases, preferably shrimp alkaline phosphatase, FastAP alkaline phosphatase, or a combination thereof.

Preferably, the crowding agent comprises polyethylene glycol and/or the lithium-containing buffer comprises lithium chloride, lithium acetate, lithium borate, or a combination thereof.

In an embodiment, the step c) comprises adding a deadenylase and a 5'-3' DNA exonuclease to the ligated product, and incubating the mixture for at least 15 minutes at about 20-35° C., and/or purification after the incubation.

In a second aspect, the present invention pertains to a method of preparing a DNA library in particular a cDNA library, comprising the steps of:
  i) producing a cDNA from a sample as described above; and
  ii) ligating the cDNA with a second adapter in the presence of a crowding agent to produce a ligated product; and amplifying the ligated product.

Preferably, the ratio of the amount of the cDNA to that of the second adapter is less than 1:2.5, or about or less than 1:5. In an embodiment, the second adapter comprises a sequence represented by SEQ ID NO: 2.

In an embodiment, the crowding agent comprises polyethylene glycol preferably having a molecular weight of more than 4,000, more than 6,000, or about 8,000.

Further, there is provided a kit for preparing a DNA library in particular a cDNA library from a sample of nucleic acids. The kit is particularly useful in the methods as described above. In particular, the kit comprises:
  a dephosphorylating agent comprising one or more alkaline phosphatases;
  a crowding agent; and
  a mixture comprising a deadenylase, a 5'-3' DNA exonuclease or a combination thereof.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

DETAILED DESCRIPTION OF THE EMBODIMENTS

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise.

Other than in the working examples, or where otherwise indicated, all numbers used herein should be understood as modified in all instances by the term "about" The term "about" when used in connection with a number can mean, for example, ±2%.

The present invention in the first aspect pertains to a method of producing a complementary DNA (cDNA) from a sample of nucleic acids, in particular a sample comprising RNAs, comprising the steps of:
 a) generating a dephosphorylated RNA from the sample;
 b) ligating the dephosphorylated RNA with a first adapter in the presence of a crowding agent to produce a ligated product;
 c) removing the excess first adapter by adding at least two enzymes; and
 d) performing reverse transcription in a lithium-containing buffer to produce the cDNA.

The sample used in the present invention comprises nucleic acids obtained from a natural source, or artificially synthesized or modified. The natural source includes, but not limited to, a mammal such as a human or a rodent, a plant, an insect, or a microorganism such as a bacterium, a virus, a fungus or the like. The sample in particular comprises a target nucleic acid which is to be used as a template to generate a cDNA. The target nucleic acid may be a single-stranded RNA sequence selected from the group consisting of an mRNA, a tRNA, an rRNA, a miRNA, ncRNA, and lncRNA, or the like. It would be appreciated that the sample may comprise more than one target nucleic acids for generating more than one cDNAs.

In an embodiment where the target nucleic acid is a RNA preferably an mRNA or ncRNA, the sample preferably comprises a fragmented RNA which has a hydroxyl group at its 5' end and a phosphate group at its 3' end. In other words, the sample preferably comprises RNA fragments in particular mRNA or ncRNA fragments. It would be appreciated that any suitable methods for fragmenting nucleic acids may be applied to the invention to produce a fragmented nucleic acid in particular a fragmented RNA.

The step a) of the method comprises generating a dephosphorylated RNA. Preferably a fragmented RNA carrying a 3' phosphate group in the sample is dephosphorylated by a dephosphorylating agent. In an embodiment, the step a) comprises:
 adding a dephosphorylating agent comprising one or more alkaline phosphatases to the sample; and
 incubating the mixture under which dephosphorylation takes place.

This dephosphorylation step facilitates the subsequent ligation between the RNA with an adapter. The term "dephosphorylating agent" refers to an agent that is capable of removing a phosphate group from a molecule preferably a nucleic acid. In an embodiment, the dephosphorylating agent of the present invention is capable of replacing the phosphate group with a hydroxyl group in particular at 3' end of the RNA. The term "alkaline phosphatase" as used herein refers to a protein enzyme which works well in alkaline environments and is capable of removing a phosphate group from a molecule. In an embodiment, the dephosphorylating agent comprises shrimp alkaline phosphatase, FastAP Thermosensitive Alkaline Phosphatase, or a combination thereof; in particular comprises shrimp alkaline phosphatase and FastAP Thermosensitive Alkaline Phosphatase.

In an embodiment, the dephosphorylating agent is devoid of a kinase such as polynucleotide kinase (PNK).

The inventors unexpectedly found that alkaline phosphatases particularly shrimp alkaline phosphatase and FastAP Thermosensitive Alkaline Phosphatase can improve the dephosphorylation of fragmented RNAs and facilitate the subsequent ligation to produce more ligated products. In an embodiment, the application of the alkaline phosphates achieves a more than 30% increase of production yield of the subsequent ligated product compared to that achieved by a kinase in particular PNK.

Preferably, the mixture of the dephosphorylating agent and the sample is incubated at about 20 to 50° C., about 30 to 40° C., about 32 to 38° C., or about 37° C. for more than 15 min, more than 30 min, or about or less than 1 h to allow the dephosphorylation to take place.

In the step b) of the method, the ligation between the dephosphorylated RNA and the first adapter is conducted in the presence of a crowding agent. The first adapter used in the method is preferably a DNA adapter, more preferably a 3' end DNA adapter, i.e. being capable of binding to the 3' end of the dephosphorylated RNA for ligation. The DNA adapter is preferably a DNA adapter with 5' pre-adenylated functional group followed by random hexamer nucleotides for efficient and unbiased ligation, as well as a C3 carbon spacer to avoid self-ligation. In an embodiment, the first adapter comprises a sequence represented by SEQ ID NO: 1, preferably comprises a 5' pre-adenylated functional group and a C3 carbon spacer for forming a sequence 5'-5rApp-NNNNNNAGATCGGAAGAGCACACGTCTG-3SpC3-3'.

Preferably, the ratio of the amount of the dephosphorylated RNA to the amount of the first adapter is less than 1:1, about or less than 1:2.5, about or less than 1:5, or about or less than 1:10. In an embodiment, the amount of the dephosphorylated RNA to the amount of the first adapter is about 1:10.

The term "crowding agent" refers to an agent comprising macromolecules which can occupy a large proportion of the volume in the mixture, and alter the equilibrium of a reaction. The crowding agent used herein is suitable for favoring the binding between a nucleic acid sequence and an adapter, wherein the nucleic acid may be a RNA or a single-stranded DNA.

In the step b), the crowding agent facilitates the ligation between the dephosphorylated RNA and the first adapter. Preferably, the crowding agent may comprise, but not limited to, polyethylene glycol (PEG), Dextran, Ficoll, polyvinyl alcohol, or the like. In an embodiment, the crowding agent comprises PEG, preferably PEG having an average molecular weight (MW) ranging from 4,000 to 10,000. For example, the PEG may be PEG 4,000, PEG 6,000, PEG 8,000, PEG 10,000 or the like. In a particular embodiment, the crowding agent comprises PEG 8,000.

Preferably, the ligation is conducted in the presence of about 1% to 30% (w/w), about 5% to 25% (w/w), about 10 to 20% (w/w), about 15 to 20%, or about 17.5% of the crowding agent.

The step c) of the method comprises a step of:
adding a deadenylase and a 5'-3' DNA exonuclease to the ligated product obtained in the step b), and incubating the mixture for at least 15 minutes at about 20-35° C.; and
optionally performing purification.

The term "deadenylase" refers to an enzyme being capable of hydrolyzing a 5'-5' pyrophosphate linkage in nucleotides. Preferably, the deadenylase is a yeast 5' deadenylase in particular derived from *Saccharomyces cerevisiae*. In an embodiment, the deadenylase may be obtained commercially with a Catalog number of M0331S from New England BioLabs Inc. The term "5'-3' DNA exonuclease" refers to an enzyme being capable of cleaving DNA nucleotides in the 5' to 3' direction. Preferably, the 5'-3' DNA exonuclease specifically targets and a single-stranded DNA sequence and removes deoxynucleotide monophosphates from the sequence. In an embodiment, the 5'-3' DNA exonuclease may be obtained commercially with a Catalog number of M0264S from New England BioLabs Inc, which may be $RecJ_f$ enzyme.

In an embodiment where the amount of the first adapter is more or significantly more than the amount of the dephosphorylated RNA, the first adapter may be in excess. The method thus comprises a step of removing the excess first adapter by utilizing a deadenylase and a 5'-3' DNA exonuclease before performing the reverse transcription of the step d). This is advantageous in that undesirable side-products such as unreacted components can be substantially minimized.

In another embodiment, the step c) further comprises purification after the incubation. The purification may be performed by using a purification column or other purification methods such as ethanol precipitation or magnetic-bead based size selection. It would be appreciated that purification column can be commercially available and selected based on the size of the ligated product.

The utilization of the digestive enzymes and/or the purification column provides a more efficient approach to remove impurities in particular for subsequent reverse transcription.

After removing the excess adapter, a reverse transcription is conducted in buffer preferably a lithium-containing buffer to produce the DNA in particular the cDNA. Preferably, the lithium-containing buffer comprises lithium chloride, lithium acetate, lithium borate, or a combination thereof. The inventors found that the lithium-containing buffer is particularly suitable for facilitating the reverse transcription of the RNA to produce the corresponding cDNA. In a particular embodiment, the lithium-containing buffer comprises lithium chloride.

A locked nucleic acid (LNA) may be used in the reverse transcription. The term "locked nucleic acid" refers to a nucleic acid having at least one modified base. The modified base has at least one extra bridge on the ribose moiety to hold the ribose ring at a particular conformation. The extra bridge may be found at 2' oxygen and 4' carbon of the ribose moiety. In this invention, the LNA may act as a primer to produce the DNA in the presence of a DNA ligase. In an embodiment, a LNA is used in the reverse transcription to produce the cDNA in the step d) of the method. Preferably, the ratio of RNA to LNA primer used in the step d) is about or less than 1:1, in particular about 1:1, about 1:2.5, about 1:5, about 1:10 or less than 1:10.

The present invention in the second aspect provides a method of preparing a DNA library. The method comprises the steps of:
i) producing the DNA in particular the cDNA from a sample as described above; and
ii) ligating the cDNA with a second adapter in the presence of a crowding agent as defined above to produce a ligated product; and amplifying the ligated product.

The second adapter used herein is preferably a DNA adapter, more preferably a 3' end DNA adapter, i.e. being capable of binding to the 3' end of the cDNA for ligation. The second DNA adapter is preferably a DNA adapter that contains a 5' phosphate group for efficient ligation, a 3' C3 carbon spacer to avoid self-ligation, and nucleotides that will be compatible for next generation sequencing purpose, i.e. the nucleotides can eventually form part of the illumine sequencer adapter or the like. In an embodiment, the second adapter may comprise a sequence represented by SEQ ID NO: 2, preferably comprise a 5' phosphate group, and a 3' C3 spacer for forming sequence 5'-5Phos-AGATCG-GAAGAGCGTCGTGTAGCTCTTCCGATCTN$_{10}$-3SpC3-3'.

Preferably, the ratio of the amount of the cDNA to that of the second adapter is less than 1:1, about or less than 1:2.5, about or less than 1:5, or about or less than 1:10. In an embodiment, the amount of the cDNA to the amount of the second adapter is about 1:10.

In the step ii), the crowding agent facilitates the ligation between the cRNA and the second adapter. Preferably, the crowding agent may comprise, but not limited to, polyethylene glycol (PEG), Dextran, Ficoll, polyvinyl alcohol, or the like. In an embodiment, the crowding agent comprises PEG, preferably PEG having an average molecular weight (MW) ranging from 4,000 to 10,000. For example, the PEG may be PEG 4,000, PEG 6,000, PEG 8,000, PEG 10,000 or the like. In a particular embodiment, the crowding agent comprises PEG 6,000, PEG 8,000 or a combination thereof.

Preferably, the DNA ligation is conducted in the presence of about 1% to 20% (w/w), about 5% to 15% (w/w), or about 7 to 13% (w/w) of the crowding agent.

In an embodiment, the ligation is conducted at a temperature of about 20-40° C. for at least 1 h.

The invention provides methods for rapid construction of a DNA in particular a cNDA and the corresponding library. The method is exceptionally suitable for preparing the DNA and its library with high yield from low input-RNA, e.g. from rare cells and tissues, or pathogenic RNAs. The side-products and/or contaminations can also be significantly reduced as compared to the currently available methods. This method is easy to operate and cost-effective.

In a further aspect, the present invention provides a kit for preparing a DNA library from a sample of nucleic acids, comprising:
 a dephosphorylating agent as described above, in particular comprising one or more alkaline phosphatases, preferably the alkaline phosphatase is selected from alkaline phosphatase, FastAP alkaline phosphatase, or a combination thereof;
 a crowding agent as described above; and
 a mixture comprising a deadenylase, a 5'-3' DNA exonuclease, or a combination thereof.

In a preferred embodiment, the kit further comprises a first adapter comprising a SEQ ID NO: 1 and/or a second adapter comprising a sequence represented by SEQ ID NO: 2. These adapters are capable of binding to an end of the corresponding nucleic acid and facilitate later reactions such as reverse transcription and PCR amplification.

Preferably, the crowding agent comprises polyethylene glycol which has an average molecular weight ranging from 4,000 to 20,000. In a particular embodiment, the crowding agent comprises or substantially comprises PEG 8,000.

The kit may further comprise one or more reverse transcriptase, and preferably the reverse transcriptase is selected from SSIII and TGIRT.

It would be appreciated that the kit may also comprise a RNA ligase, a DNA ligase, or a combination thereof. The person skilled in the art is aware of possible RNA ligases and/or DNA ligases for the present invention.

In addition, the kit may further comprise a LNA for conducting the reverse transcription, and in particular the LNA acts as a primer to produce the desired DNA. The inventors unexpectedly found that the application of LNA in reverse transcription significantly enhances the yield of DNA products.

In an embodiment, the kit further comprises a lithium-containing buffer as described above. Preferably, the lithium-containing buffer comprises lithium chloride, lithium acetate, lithium borate, or a combination therefore; more preferably, the lithium-containing buffer comprises lithium chloride. In a particular embodiment, the kit comprises a buffer mixture containing Tris buffer, magnesium chloride ($MgCl_2$), dithiothreitol (DTT), dNTPs, and lithium chloride (LiCl).

It would be appreciated that the methods and kit as provided in this invention can be applied in various applications, including genome studies such as RNA expression, RNA structurome, RNA interactome, RNA epigenetics studies and sequencing, medical applications such as diseases diagnosis and treatment, transgenic application and the like.

The invention described herein is susceptible to variations and modifications other than those specifically described. The invention includes all such variations and modifications. The invention also includes all steps and features referred to or indicated in the specification, individually or collectively, and any and all combinations of the steps or features. Any reference to prior art contained herein is not to be taken as an admission that the information is common general knowledge, unless otherwise indicated.

Example 1

Dephosphorylation of Alkaline Phosphatase

Polynucleotide kinase (PNK) is a common enzyme used for dephosphorylating RNAs in high profile RNA structurome studies. However, it was found that the dephosphorylation efficiency of PNK is not satisfactory in particular for analyzing low-abundant RNAs. The inventors derived new strategy to improve the efficiency of dephosphorylation by utilizing alkaline phosphatases. A test was conducted to determine the dephosphorylation efficiency of alkaline phosphatases over random 40 nucleotides which have a 3' phosphate group (denoted as $N_{40}$-3'P), and compared with that of PNK. The dephosphorylation efficiency is determined based on the yield of ligated product obtained after the dephosphorylation and the subsequent ligation with a DNA adapter. The determination was conducted via polyacrylamide gel electrophoresis (PAGE).

Figure 1A:
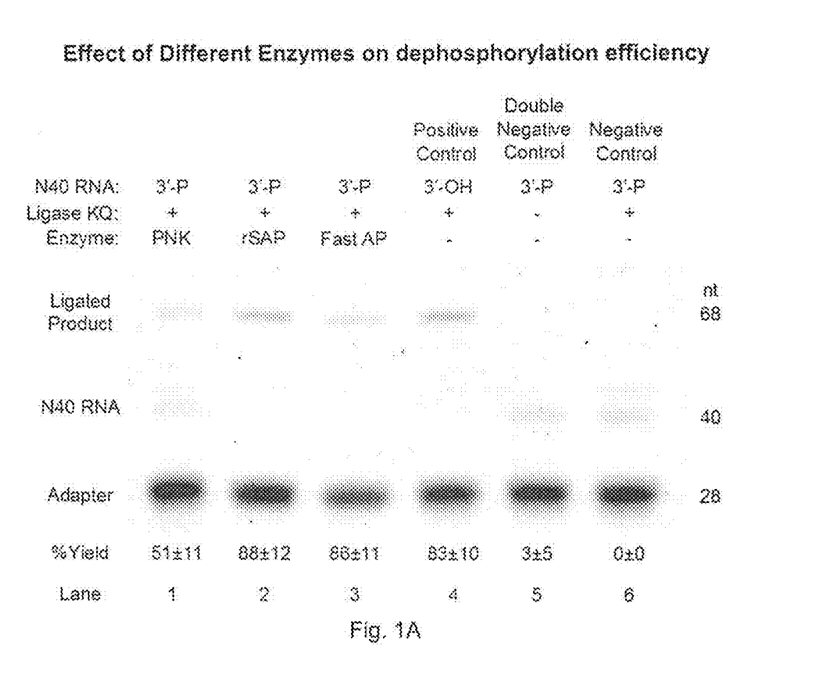
FIG. 1A is a picture obtained from PAGE analysis on the ligated products produced after dephosphorylating random RNAs (N40 RNA) with enzymes PNK, rSAP and Fast AP, followed by ligation as the readout, wherein the respective conditions are shown above the picture.
Figure 1B:
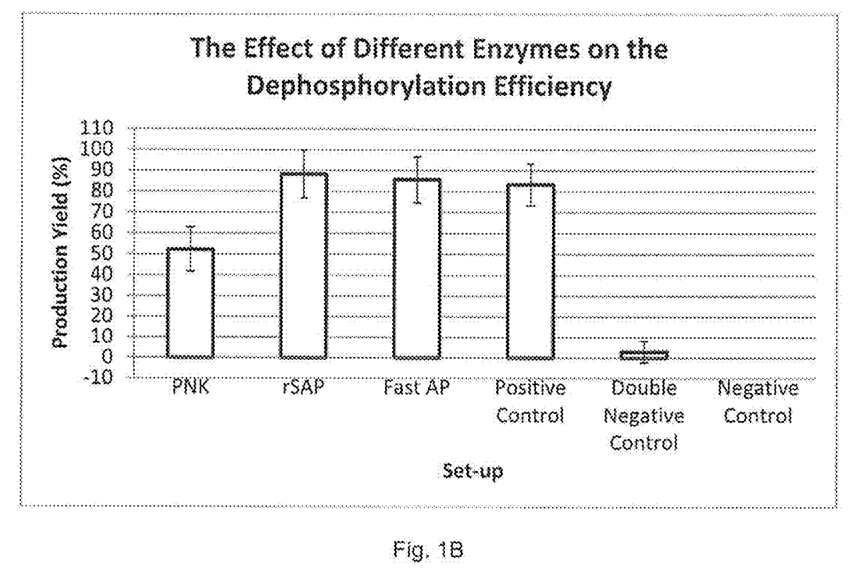
FIG. 1B is a plot showing the production yield of ligated products produced under different treatments as indicated in FIG. 1A.

Particularly, three enzymes, T4 PNK, shrimp alkaline phosphatase (denoted as rSAP) and FastAP Thermosensitive Alkaline Phosphatase (denoted as Fast AP) were tested under PNK buffer condition. Each of the enzymes was incubated with the random nucleotides performed at 37° C. for 30 min. Positive control and negative controls were set up. Positive control was conducted by ligating the $N_{40}$-3'-OH RNA with the 3'-rApp adapter without dephosphorylation. After dephosphorylation, the 40 nt RNA was ligated to the 28 nt 3'-rApp adapter to show the 68 nt ligation product. Since the adapter only ligates to the RNA with 3'-OH end, the intensity of ligation product could reflect the efficiency of the enzymes—the higher the production yield, the higher the efficiency of the enzyme. Two negative controls were also introduced, either no dephosphatase was added (Negative Control) or both dephosphatase and ligase were not added (Double Negative Control). The results are shown in FIGS. 1A and 1B. Errors shown were standard deviations. n=3. nt=nucleotide.

As shown in FIGS. 1A and 1B, PNK enzyme only achieved about 50% dephosphorylation, whereas both rSAP and Fast AP enzymes achieved >80% dephosphorylation efficiency, i.e. a dramatic increase of 30% or above compared to PNK. This unexpected increase demonstrates that alkaline phosphatases in particular shrimp alkaline phosphatase, FastAP Thermosensitive Alkaline Phosphatase can provide more dephosphorylated RNAs for subsequent ligation, and thus reduce the loss of RNAs materials and increase the yield of the ligated product. It is particularly suitable for nucleic acid studies on low-abundant nucleic acids such as low-abundant RNAs. In addition, the costs of rSAP and Fast AP per reaction are much cheaper than PNK.

Example 2

Figure 2A:
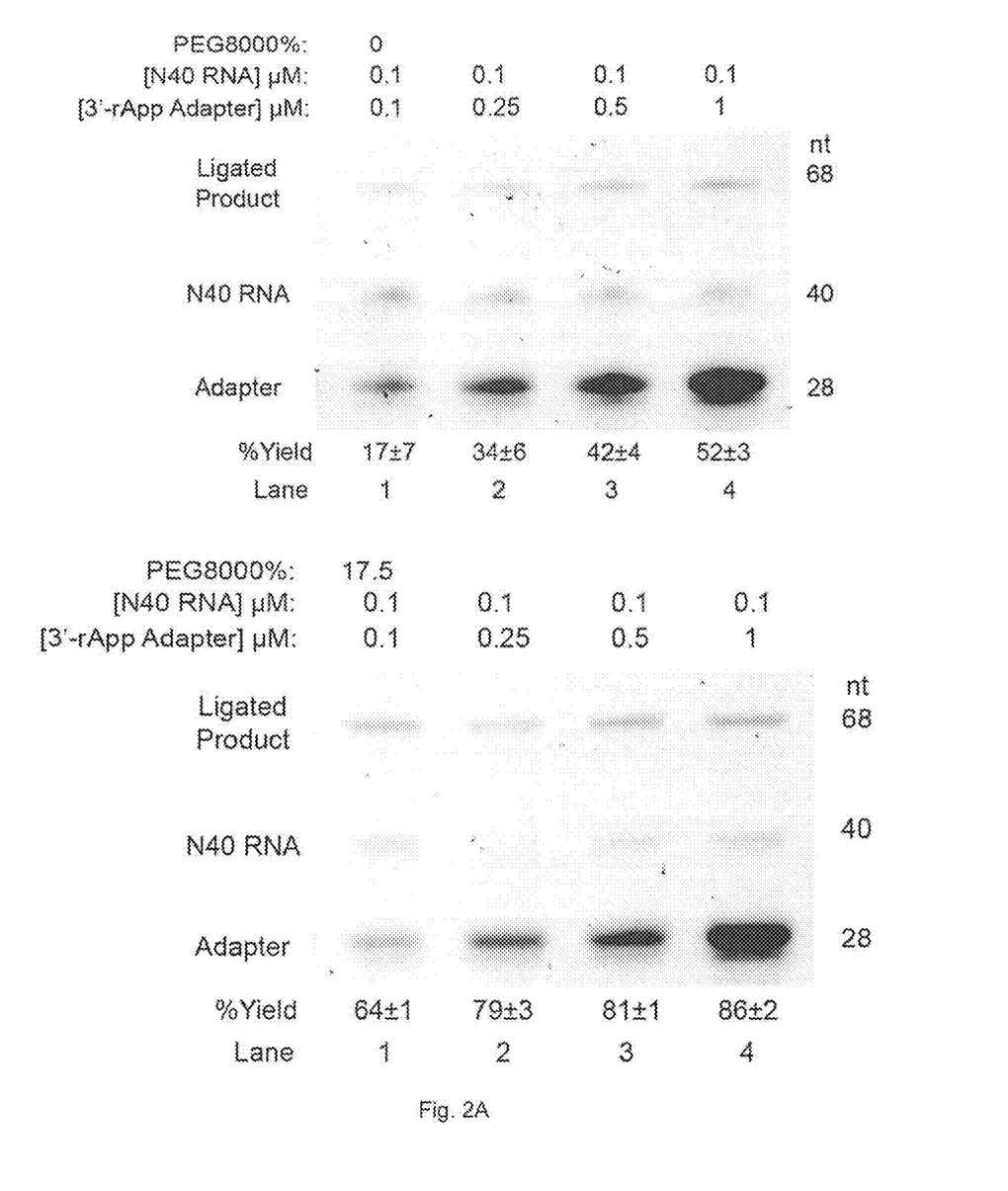
FIG. 2A includes 2 pictures obtained from PAGE analysis on the ligated products produced after ligating the dephosphorylated RNAs (N40 RNA) with a DNA adapter, under various ratios of the amount of the dephosphorylated RNAs to that of the adapter, in the presence or absence of 17.5% (w/w) PEG 8,000, wherein the respective conditions are shown above the pictures.
Figure 2B:
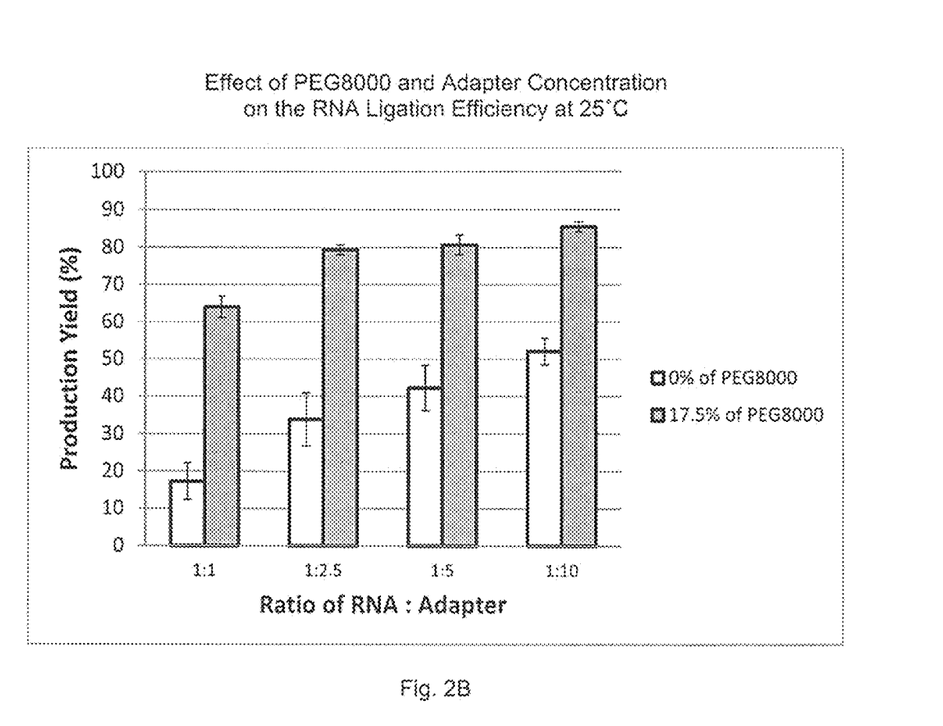
FIG. 2B is a plot showing the production yield of ligated products produced under different treatments as indicated in FIG. 2A.

Effects of a Crowding Agent and the Concentration of the First Adapter on RNA Ligation After dephosphorylation, an 3' DNA adapter can be used to ligate to the dephosphorylated RNA in the presence of a RNA ligase, for example a T4 RNA ligase 2 KQ, so as to form a common handle which can be used in the subsequent reverse transcription step. To improve the ligation yield, a crowding agent in particular polyethylene glycol (PEG) is utilized in the method. A test was conducted to evaluate the effect of PEG 8,000 on RNA ligation. The reactions were performed for an hour only at ambient temperature (25° C.). The results are shown in FIGS. 2A and 2B. The panels showed the efficiency of 3'-RNA ligation performed by T4 RNA Ligase 2, truncated KQ with either (A) 0% of PEG8000 or (B) 17.5% of PEG8000. The 40 nt size RNA was ligated with the 28 nt size 3'-rApp adapter in four final concentrations, leading the RNA:Adapter ratio to be 1:1, 1:2.5, 1:5 and 1:10, as shown in lane 1-4 respectively. The size of the ligated product was therefore expected to be 68 nt. The production yield enhanced with increasing concentration and PEG8000 percentage as indicated. Errors shown were standard deviation. n=3. nt=nucleotide.

There is an increase of more than 30% when the ligation was conducted in the presence of 17.5% PEG 8,000, compared to that conducted in the absence of PEG 8,000, while other factors remained the same. Further, based on the results in FIG. 2B, the inventors found that there is a promising improvement in the RNA ligation efficiency when the ratio of the dephosphorylated RNA to the DNA adapter is adjusted from 1:1 to 1:10, in particular the RNA ligation efficiency soared from about 64% (1:1 ratio) to 86% (1:10 ratio).

These results prove that adding a crowding agent and using a higher ratio of adapter to RNA can produce more ligated products, thereby substantially improving the ligation efficiency.

Example 3

Removal of Excess Adapters Using Enzymatic Digestion

In an example where the ratio of RNA to the first adapter in the RNA ligation step is 1:10, the first adapter is used in excess. It is necessary to remove the unreacted adapter before moving on to the next step, in particular to avoid accumulation of undesirable side-products that might affect the analysis and downstream reactions. Currently, polyacrylamide gel may be generated to select the target ligated product. However, this approach is time-consuming and is susceptible to contamination. Also, gel extraction generally has poor recovery yield.

Figure 3A:
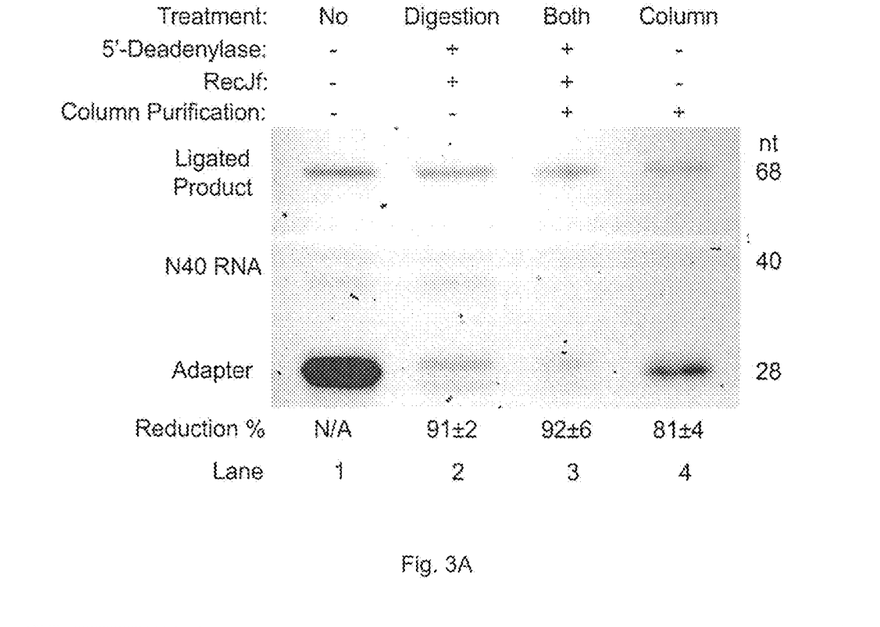
FIG. 3A is a picture obtained from PAGE analysis on the ligated products and the adapter remained after conducting enzymatic digestion and/or purification using purification column, wherein the respective conditions are shown above the picture.
Figure 3B:
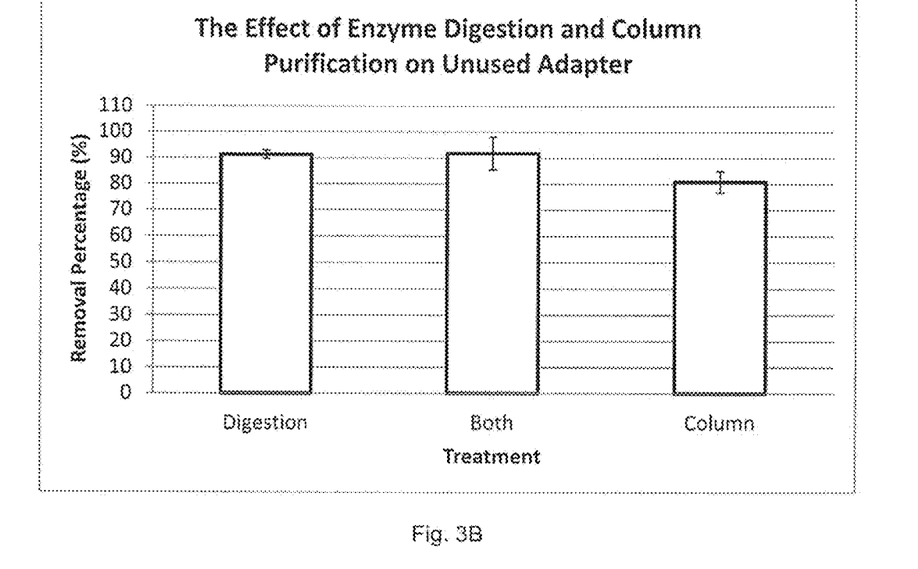
FIG. 3B is a plot showing the removal percentage of the excess adapter under different treatments as indicated in FIG. 3A.

In this method, two enzymes—a deadenylase and a 5' to 3' DNA exonuclease are applied to digest the excess adapters, preferably followed by a purification step using a purification column to remove the residual adapters and to clean up the sample for subsequent reverse transcription. A test was conducted to demonstrate the efficiency of the enzymes in removing the excess adapters. In particular, a mixture containing the enzymes and ligated products obtained in Example 2 was incubated at 30° C. for 30 min, with or without subsequent purification. A mixture containing the ligated products only was also subject to purification column. The removal efficiency of the excess adapter was then determined based on the amount of adapter left. The results are shown in FIGS. 3A and 3B. The effectiveness of these three approaches to remove or eliminate the unused 3'-adapter, i.e. enzyme digestion (lane 2), column purification (lane 4) and column purification after enzyme digestion (lane 3), were shown. As compared with lane 1 which did not involve any treatments, the three approaches reduced more than 80% of excess adapters. The reduction percentage of each treatment was shown with the standard deviations indicated.

As shown in FIGS. 3A and 3B, the addition of the enzymes allows the digestion of the excess adapters and achieves a removal efficiency of about 91% without a purification step using the purification column. When both the enzymes and purification column were used, the removal efficiency reaches about 92%, i.e. almost all of the excess adapters were removed from the mixture. The efficiency achieved by the enzymes is better than using purification column alone—about 80% of removal efficiency. Further, the application of the enzymes is a faster approach to remove the undesirable impurities from the mixture.

Example 4

Performing Reverse Transcription

After the purification in Example 3, the ligated RNA-adapter is subject to reverse transcription. A test was conducted to evaluate the efficiency and identify the reverse transcriptase that performs best.

An RNA containing a G-quadruplex structure (thermostable RNA secondary structure) was used in a test to determine the reverse transcription efficiency of different reverse transcriptases in, respectively, potassium-containing buffer, lithium-containing buffer and a commercial buffer (denoted as ventor) provided/recommended by the corresponding vendor. Specifically, the potassium-containing buffer contains 20 mM Tris buffer at a pH of 7.5, 4 mM magnesium chloride ($MgCl_2$), 1 mM dithiothreitol (DTT), 1 mM dNTPs, and 150 mM potassium chloride (KCl). The lithium-containing buffer contains 20 mM Tris buffer at a pH of 7.5, 4 mM $MgCl_2$, 1 mM DTT, 1 mM dNTPs, and 150 mM lithium chloride (LiCl). The commercial buffer having TGIRT®-III reverse transcriptase (TGIRT) contains 1× reaction with 450 mM sodium chloride (NaCl), 5 mM $MgCl_2$, 20 mM Tris-HCl at pH 7.5. The commercial buffer having SuperScript® III reverse transcriptase (SS III) contains 1× First-strand buffer with 50 mM Tris-HCl at pH 8.3, 75 mM KCl, and 3 mM $MgCl_2$. The commercial buffer having ProtoScript II reverse transcriptase contains 1× reaction buffer with 50 mM Tris-HCl at pH 8.3, 75 mM KCl, and 3 mM $MgCl_2$.

Figure 4A:
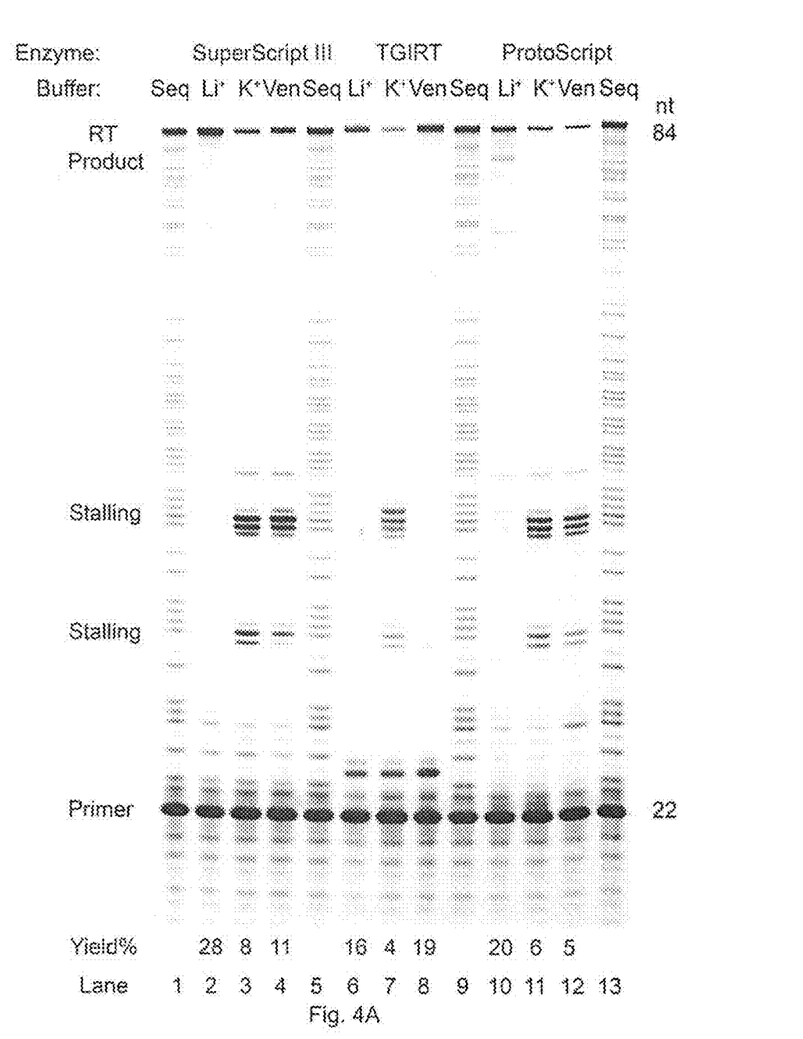
FIG. 4A is a picture obtained from PAGE analysis on the cDNA products after conducting reverse transcription on 149 wild-type (84 nt) RNA using different reverse transcriptases including SuperScript® III reverse transcriptase (SS III), TGIRT®-III reverse transcriptase (TGIRT) and ProtoScript II reverse transcriptase (ProtoScript), and in different buffers including Li-containing buffer, K-containing buffer, and commercial buffer (provided/recommended by vendor). The respective conditions are shown in the figure.
Figure 4B:
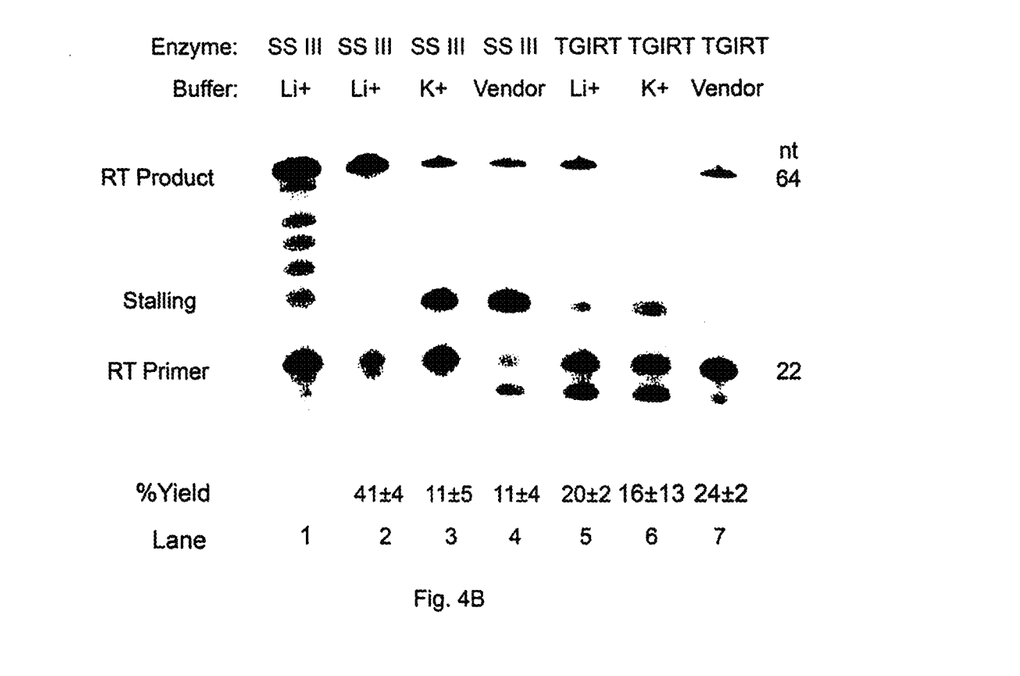
FIG. 4B is a picture obtained from PAGE analysis on the cDNA products after conducting reverse transcription on TERRA (64 nt) RNA using different reverse transcriptases including SuperScript® III reverse transcriptase (SS III), TGIRT®-III reverse transcriptase (TGIRT) and ProtoScript II reverse transcriptase (ProtoScript), and in different buffers including Li-containing buffer, K-containing buffer, and commercial buffer (provided/recommended by vendor). The respective conditions are shown in the figure. The error shown was standard deviation; nt=nucleotides; n=3.

The ion-containing buffers were used to determine the existence of stalling when transcribing cDNA from RNA. The stalling exists when the transcriptase fails to pass through the secondary structure, G-quadruplex, and stops the transcription at the middle of the sequence. Two in vitro-transcribed RNA G-quadruplex-containing transcripts were used in the test—149 wild-type (84 nt) and TERRA (64 nt). With reference to FIGS. 4A and 4B, the position of stalling is located in the G-rich region, which is the location of the G-quadruplex. In both types of RNA, stalling bands were observed in the K+ containing buffer regardless the enzyme used. Without wishing to be limited by theory, it is believed that $K^+$ containing buffer has an effect in stabilizing G-quadruplex, and reverse transcriptase does not work well to overcome RNA secondary structure such as G-quadruplex. The results confirm the effect of K+ containing buffer in reverse transcription.

In contrast, there is no stalling band observed in reaction conducted in $Li^+$ containing reaction buffer which is believed to have slight or no G-quadruplex stabilizing effect. The reactions conducted using SS III and Protoscript also produce more full-length bands. For SS III and ProtoScript, no stalling were observed in Li+ containing buffer, but stalling was observed in the vendor buffer. For TGIRT, no stalling was observed in Li+ and vendor buffer for the reactions done by 149 wild-type, while there was stalling shown in the Li+ containing buffer for TERRA. The combination of TGIRT and commercial buffer alleviates the reverse transcriptase stalling. As reflected from the percentage yield, SS III gave a higher percentage of cDNA product compared with TGIRT and ProtoScript. Reverse transcriptase SSIII achieved the best results, with 28% under $Li^+$-containing buffer.

Figure 4C:
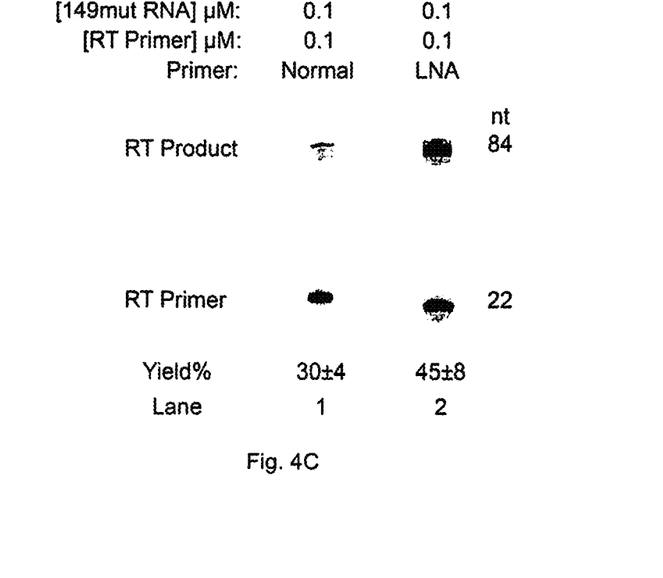
FIG. 4C is a picture obtained from PAGE analysis on the cDNA products after conducting reverse transcription on 149 mut-type RNA using different DNA primers—LNA primer and normal primer having SEQ ID NO. 3. nt=nucleotide; n=3.
Figure 4D:
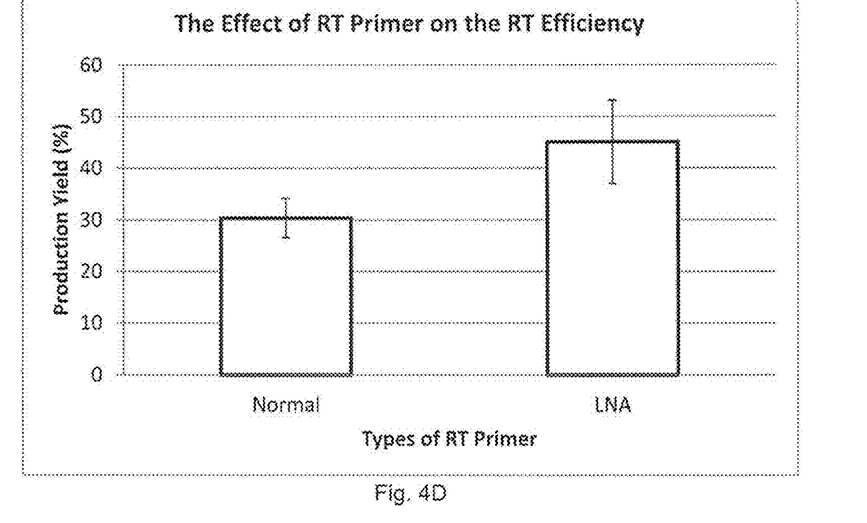
FIG. 4D is a plot showing the production yield (%) of the cDNA products based on the PAGE results in FIG. 4C, n=3.
Figure 4E:
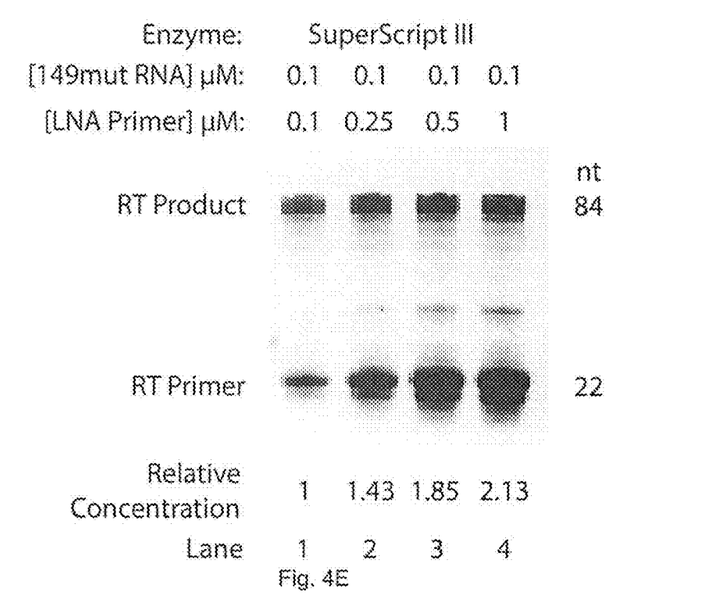
FIG. 4E is a picture obtained from PAGE analysis on the cDNA products after conducting reverse transcription on 149 mut-type RNA using LNA primer at different concentration ratio (n=3).

With reference to FIGS. 4C and 4D, 22 nucleotides long RT primer with locked nucleic acid (LNA) incorporated in the sequence 5'-TYE665-aAcCgCACCGAAGCGCG-3' (locked sequence of SEQ ID NO. 3, which the location of LNA base was denoted with small letters). The location of LNA base was denoted with small letter. The LNA primer was added to the Li+ containing buffer and SuperScript III containing buffer. The normal primer sequence having a sequence of SEQ ID NO. 3 (5'-Cy5-AACCGCACCGAAGCGCG-3') does not contain any LNA bases. The normal primer sequence was used as comparison. The efficiency of the normal DNA primer (lane 1) and the DNA primer with LNA (lane 2) were compared. It was found that DNA primer with LNA generated higher percentage of yield of cDNA in 1:1 ratio. The results then shed some lights on the effect of the RNA to primer ratio on the RT efficiency. With reference to FIG. 4E, different concentrations of LNA primer were added to react with 0.1 pmol of RNA to generate different RNA-to-primer ratio, which are 1:1, 1:2.5, 1:5 and 1:10 shown in lanes 1-4 of FIG. 4E respectively. After dividing the production yield with that obtained from 1:1 ratio, the relative concentration of each ratio was obtained. As reflected from the relative concentration, the inventors conclude that the lower the ratio between RNA and LNA primer, the higher the cDNA production yield.

Example 5

DNA Ligation

Once cDNA is generated, a second adapter can be introduced via single-stranded DNA (ssDNA) ligation to form another handle on the cDNA for subsequent PCR amplification. The inventors utilized a second adapter having a sequence represented by SEQ ID NO: 2.

Figure 5A:
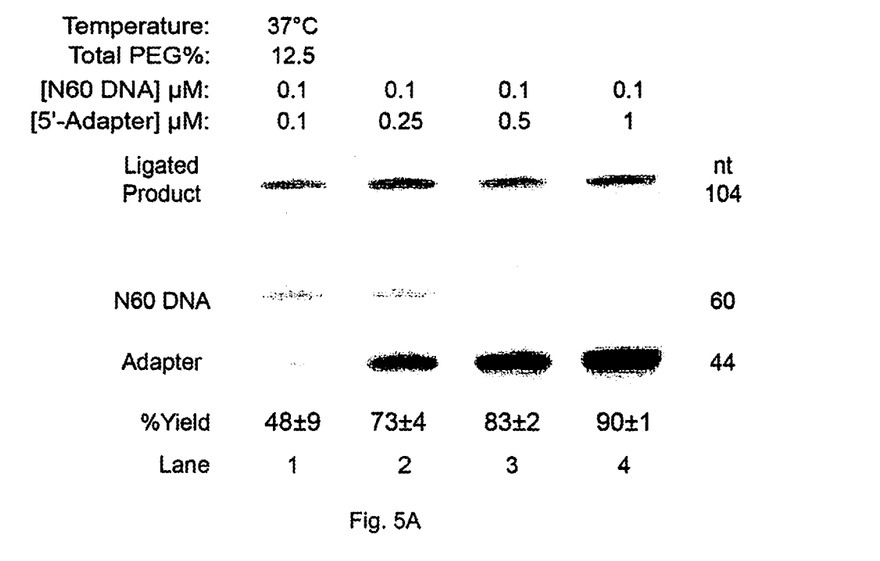
FIG. 5A is a picture obtained from PAGE analysis on the ligated products (ssDNA) after ligating the cDNA product with a 3' second adapter under different ratio of cDNA product to the adapter, and in the presence of 12.5% (w/w) PEG. The respective conditions are shown in the figure.
Figure 5B:
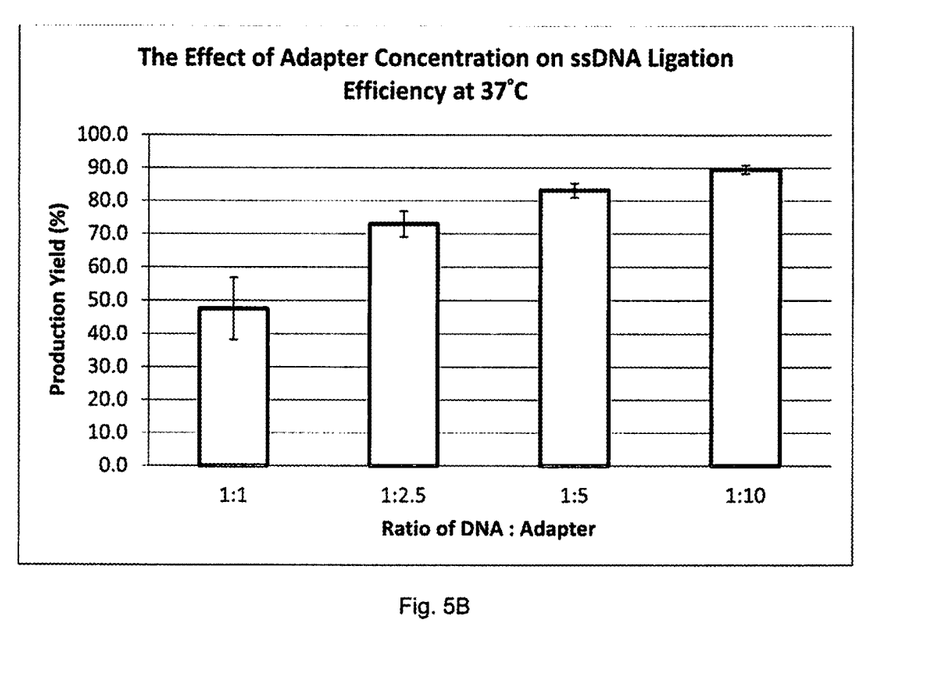
FIG. 5B is a plot showing the production yield of the ssDNA under different treatments as indicated in FIG. 5A.

In this example, the inventors determined the appropriate conditions for the DNA ligation. In particular, the ligation efficiency of different ratios of the amount of the cDNA to that of the second adapter was determined. Referring to FIGS. 5A and 5B, there is shown that when the ratio of the amount of the cDNA to that of the second adapter decreases, the production yield of the ligated product increases. The effects of temperature, PEG and 5'-adapter concentration on the ssDNA ligation efficiency are shown in FIGS. 5A and 5B. The 60 nt long single stranded DNA was ligated with the 5' adapter sized 44 nt to give a 104 nt ligated product by T4 DNA ligase. Four different final concentrations of 5'-adapter, 0.1, 0.25, 0.5 and 1 μM in lane 1-4 was used to ligate with the N60 DNA. The production yield increased with increasing 5'-adapter concentration. Thus, it is the ratio of preferably to be less than 1:1, 1:2.5, 1:5 or 1:10 for ligation between the cDNA and the second adapter.

Figure 6A:
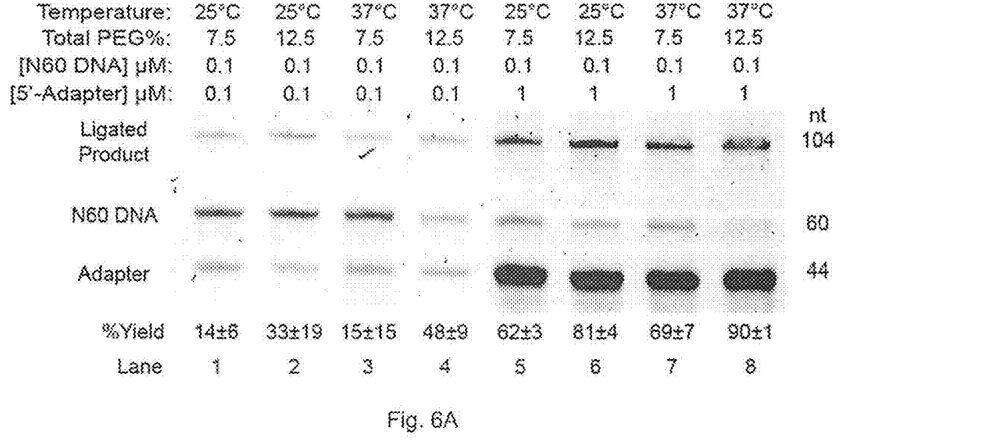
FIG. 6A is a picture obtained from PAGE analysis on the ssDNA after ligating the cDNA product with the 3' adapter under different conditions, in particular at a temperature of 25° C. or 37° C., with different cDNA to adapter ratio and in the presence of 7.5% (w/w) or 12.5% (w/w) of crowding agent PEG (a mixture of 6,000 and 8,000). The respective conditions are shown in the figure.
Figure 6B:
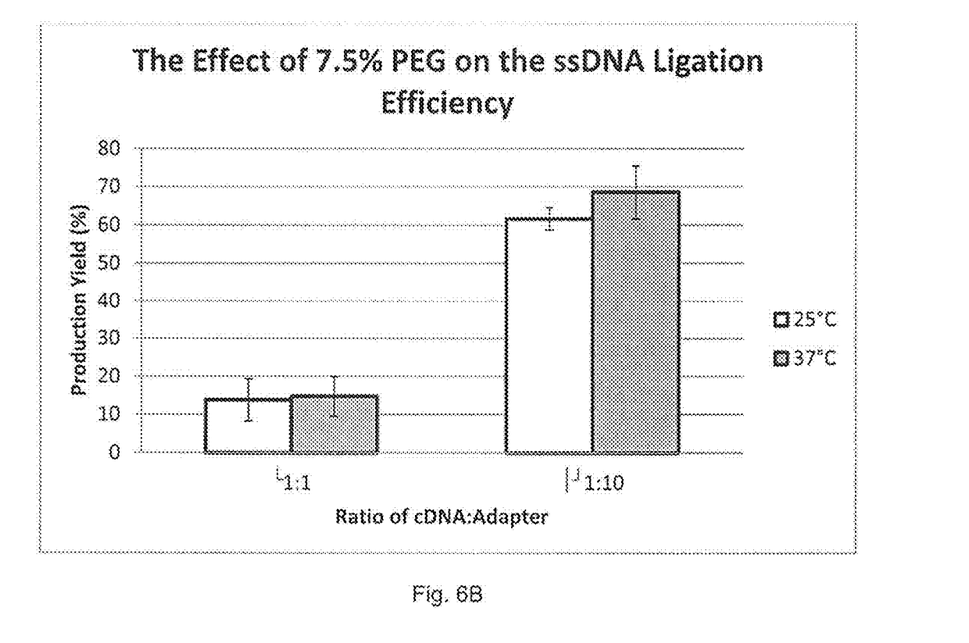
FIG. 6B is a plot showing the production yield of the ssDNA after ligating the cDNA with the adapter at 25° C. or 37° C., in the presence of 7.5% (w/w) PEG 6,000.
Figure 6C:
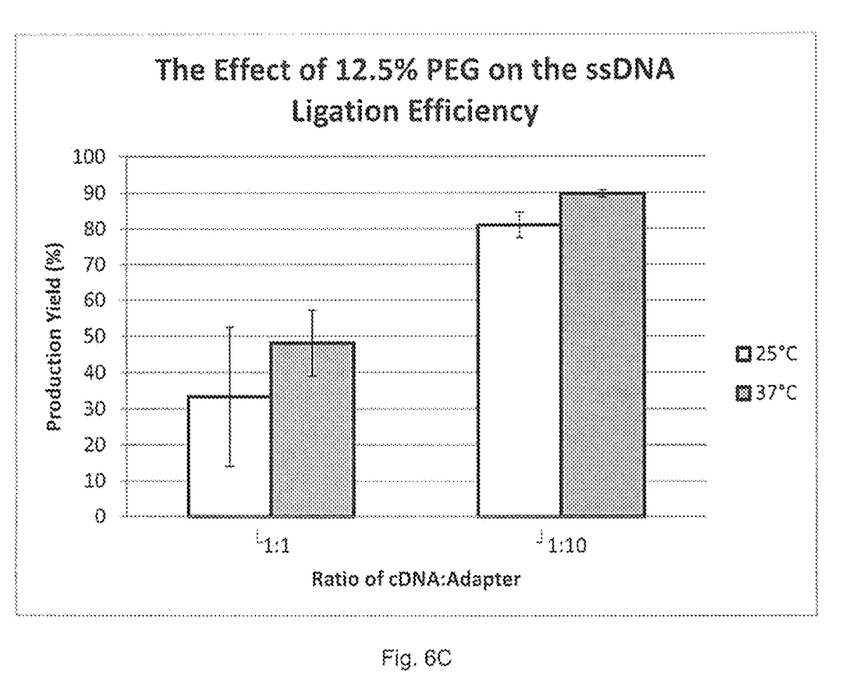
FIG. 6C is a plot showing the production yield of the ssDNA after ligating the cDNA with the adapter at 25° C. or 37° C., in the presence of 12.5% (w/w) PEG which contains 7.5% (w/w) PEG6,000 and 5% PEG8,000.

7.5% PEG 6,000 (denoted 7.5% PEG herein) or 12.5% of a mixture of PEG (contains 7.5% PEG6,000 and 5% PEG8,000, denoted as 12.5% PEG herein) was applied as a crowding agent. A PAGE was prepared based on various conditions as shown in FIG. 6A. FIGS. 6A and 6B shows the effects of temperature and percentage of PEG on the ligation efficiency. The reaction temperature was set to be 25° C. or 37° C. with 7.5% or 12.5% of PEG for the single strand DNA ligation. The efficiency enhanced with higher reaction temperature and PEG concentration. The production yields of each lane in both panels were indicated with error (standard deviation) shown. n=3. nt; nucleotides. With reference to FIG. 6A, there is an increase of the ligation efficiency for more than 30% when the ratio of the amount of cDNA to that of the second adapter is 1:10 compared to the ratio 1:1, while other factors are the same. Referring to FIGS. 6B and 6C, the ligation is improved when there is an increase of the concentration of PEG and in the reaction temperature. Accordingly, in one example of the invention, the method is conducted with the addition of 12.5% (w/w) PEG at 37° C. for about 2 h, while the ratio of the amount of cDNA to the second adapter is 1:10.

The invention claimed is:

1. A method of preparing a DNA library, comprising the steps of:
   i) producing a cDNA from a sample with the following steps:
      a) generating a dephosphorylated RNA from the sample;
      b) ligating the dephosphorylated RNA with a first adapter in the presence of a crowding agent to produce a ligated product;
      c) removing the excess first adapter by adding at least two enzymes; and
      d) performing reverse transcription in a lithium-containing buffer to produce the cDNA; and
   ii) ligating the cDNA with a second adapter in the presence of a crowding agent to produce a ligated product, wherein the second adapter comprises a sequence represented by SEQ ID NO: 2; and amplifying the ligated product.

2. The method of claim 1, wherein the ratio of the amount of the cDNA to that of the second adapter is less than 1:2.5.

3. The method of claim 1, wherein the ratio of the amount the cDNA to that of the second adapter is about or less than 1:5.

4. The method of claim 1, wherein the crowding agent has a concentration of about 1% to 20% (w/w).

5. The method of claim 1, wherein the crowding agent comprises PEG 8,000, PEG 6,000 or a combination thereof.

6. The method of claim 1, wherein the ligation in step (ii) is conducted at a temperature of about 20-40° C. for at least 1 h.

7. A kit for preparing a DNA library from a sample of nucleic acids, comprising:
   a dephosphorylating agent comprising one or more alkaline phosphatases;
   a crowding agent;
   a mixture comprising a deadenylase, a 5'-3' exonuclease, or a combination thereof; and
   a second adapter comprising a sequence represented by SEQ ID NO: 2.

8. The kit of claim 7, further comprises a first adapter comprising a SEQ ID NO: 1.

9. The kit of claim 7, wherein the dephosphorylating agent comprises shrimp alkaline phosphatase, FastAP alkaline phosphatase, or a combination thereof.

10. The kit of claim 7, further comprises a locked nucleic acid.

11. The method of claim 1, wherein the step a) comprises:
    adding a dephosphorylating agent comprising one or more alkaline phosphatases to the sample; and
    incubating the mixture under which dephosphorylation takes place.

12. The method of claim 11, wherein the dephosphorylating agent comprises shrimp alkaline phosphatase, FastAP Thermosensitive Alkaline Phosphatase, or a combination thereof.

13. The method of claim 1, wherein the crowding agent comprises polyethylene glycol.

14. The method of claim 1, wherein in the step b), the ratio of the amount of the dephosphorylated RNA to the amount of the first adapter is about or less than 1:2.5.

15. The method of claim 1, wherein in the step b), the ratio of the amount of the dephosphorylated RNA to that of the first adapter is about or less than 1:5.

16. The method of claim 1, wherein the step c) comprises:
    adding a deadenylase and a 5'-3' DNA exonuclease to the ligated product, and incubating the mixture for at least 15 minutes at about 20-35° C.

17. The method of claim 16, wherein the step c) further comprises purification after the incubation, wherein the purification is performed by using a purification column.

18. The method of claim 1, wherein the lithium-containing buffer comprises lithium chloride, lithium acetate, lithium borate, or a combination thereof.

19. The method of claim 1, wherein in the step d), a locked nucleic acid is used in the reverse transcription to produce the cDNA.

* * * * *

SEQUENCE LISTING

```
<160> NUMBER OF SEQ ID NOS: 3

<210> SEQ ID NO 1
<211> LENGTH: 28
<212> TYPE: DNA
<213> ORGANISM: Artificial Sequence
<220> FEATURE:
<223> OTHER INFORMATION: Synthesized
<220> FEATURE:
<221> NAME/KEY: misc_feature
```

```
<222> LOCATION: (1)..(6)
<223> OTHER INFORMATION: n is a, c, g, or t

<400> SEQUENCE: 1
nnnnnnagat cggaagagca cacgtctg                                           28

<210> SEQ ID NO 2
<211> LENGTH: 44
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (35)..(44)
<223> OTHER INFORMATION: n is a, c, g, or t

<400> SEQUENCE: 2
agatcggaag agcgtcgtgt agctcttccg atctnnnnnn nnnn                         44

<210> SEQ ID NO 3
<211> LENGTH: 17
<212> TYPE: DNA
<213> ORGANISM: Artificial Sequence
<220> FEATURE:
<223> OTHER INFORMATION: Synthesized

<400> SEQUENCE: 3
aaccgcaccg aagcgcg                                                       17
```